United States Patent [19]

Kondo et al.

[11] Patent Number: 4,500,733
[45] Date of Patent: Feb. 19, 1985

[54] PROCESS FOR PREPARING DIHALOVINYLCYCLOPROPANECARBOXYLIC ACIDS

[75] Inventors: Kiyoshi Kondo; Kiyohide Matsui, both of Kanagawa, Japan

[73] Assignee: Sagami Chemical ResearchCenter, Tokyo, Japan

[21] Appl. No.: 466,182

[22] Filed: Feb. 14, 1983

Related U.S. Application Data

[63] Continuation of Ser. No. 935,190, Aug. 21, 1978, abandoned, and Ser. No. 731,195, Oct. 12, 1976, abandoned.

[30] Foreign Application Priority Data

Oct. 30, 1975 [JP] Japan ................... 50-131254

[51] Int. Cl.³ .......................................... C07C 69/743
[52] U.S. Cl. ................................ 562/506; 560/102; 560/118; 560/124; 562/492; 562/500
[58] Field of Search .................. 560/124, 118, 102; 562/506, 492, 500

[56] References Cited

U.S. PATENT DOCUMENTS

| 3,123,629 | 3/1964 | Julia | 560/124 |
| 3,354,196 | 11/1967 | Julia | 560/124 |
| 3,658,879 | 4/1972 | Julia | 560/124 |
| 4,000,180 | 12/1976 | Punja | 560/124 |

OTHER PUBLICATIONS

Morrison, et al., "Organic Chemistry," 2nd ed., pp. 940–941, (1966).
Parham, "Syntheses and Reactions in Organic Chemistry," p. 216.

*Primary Examiner*—Michael L. Shippen
*Attorney, Agent, or Firm*—H. Robinson Ertelt

[57] ABSTRACT

A cyclopropanecarboxylic acid of the formula

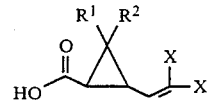

is prepared by the reaction of a compound of the formula

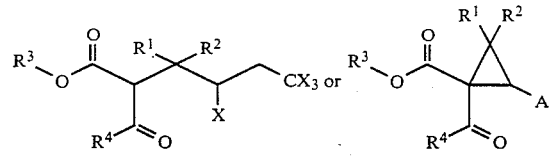

with an alkali metal hydroxide or alkaline earth metal hydroxide in an ether type solvent. $R^1$, $R^2$, and $R^4$ each independently is hydrogen or a hydrocarbon residue, $R^3$ is hydrogen or lower alkyl, X is halogen, and A is $-CH_2-CX$, 3 or $-CH=CX_2$.

11 Claims, No Drawings

PROCESS FOR PREPARING DIHALOVINYLCYCLOPROPANECARBOXYLIC ACIDS

This application is a continuation of application Ser. No. 935,190, filed Aug. 21, 1978, ans Ser. No. 731,195 filed on Oct. 12, 1976, now both abandoned.

This invention relates to a process for preparing a 2-(2,2-dihalovinyl)cyclopropanecarboxylic acid of the formula (I)

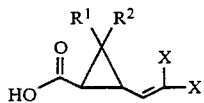

wherein $R^1$ and $R^2$ each represents a hydrogen atom or a hydrocarbon residual group, and X represents a halogen atom.

More specifically, this invention relates to a process for preparing a 2-(2,2-dihalovinyl)cyclopropanecarboxylic acid of the formula (I) above using, as a starting material, (a) an α-acyl-γ-halocarboxylic acid derivative of the formula (II)

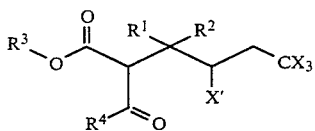

wherein $R^1$ and $R^2$ each represents a hydrogen atom or a hyrocarbon residual group, for example, a lower alkyl group, a lower cycloalkyl group, an aryl group, such as phenyl, or an aralkyl group, such as benzyl, $R^3$ represents a hydrogen atom or a lower alkyl group, $R^4$ represents a hydrogen atom, a lower alkyl group, or a phenyl group, X represents a halogen atom, and X' is a halogen, preferably bromine or chlorine, having an atomic number equal to or greater than X;

(b) a 1-acyl-2-(2,2-dihalovinyl)cyclopropane derivative of the formula (III)

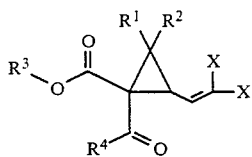

wherein $R^1$, $R^2$, $R^3$, $R^4$ and X are as defined above; or (c) a 1-acyl-2-(2,2-trihaloethyl)cyclopropane derivative of the formula (IV)

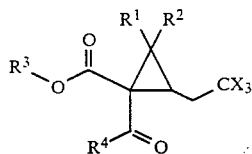

wherein $R^1$, $R^2$, $R^3$, $R^4$ and X are as defined above. The term "lower" modifying alkyl or cycloalkyl means 1 to 6 carbon atoms, preferably 1 to 4 carbon atoms.

The cyclopropanecarboxylic acids represented by the formula (I) above represent the acid moieties of synthetic pyrethroid compounds which are of interest owing to their utility as insecticides having low mammalian toxicity and long-lasting insecticidal activity [M. Elliott et al., Nature, 246, 169 (1973)].

Previously known methods for the synthesis of compounds of this type include (1) a method starting with natural chrysanthemic acid [Belgian Pat. Nos. 800,006 and 818,811 and D. G. Brown et al., J. Agr. Food Chem., 21, 767 (1973)], (2) a method comprising an addition reaction of a diazoacetic acid ester to a dihalobutadiene [J. Farkas et al., Coll. Czech. Chem. Comm., 24, 2230 (1959)], and (3) a method using, as a starting material, a 3,3-dimethyl-4-pentenoate obtainable by condensing 3-methyl-2-buten-1-ol with an orthocarboxylate [Japan Chemical Association, The 31st Autumn Annual Meeting, Preliminary Papers of Lecture Vol. I, 4A04, p. 58 (1974)]. However, neither method (1) nor method (2) is considered to be advantageous, since each requires an expensive starting material and a number of synthetic steps as well as expensive reagents. Also, method (3), which is similar to the process of this invention, is not advantageous in that it requires orthocarboxylates which are not easily available as chemical industrial raw materials.

As a result of extensive studies to eliminate the disadvantages associated with the earlier methods, a general process has been found for preparing cyclopropanecarboxylic acids having a dihalovinyl group, a process which can be advantageously practiced on an industrial scale.

The present invention provides a process for preparing directly 2-(2,2-dihalovinyl)cyclopropanecarboxylic acids by treating a β-keto-carboxylic acid derivative represented by the formula (II), (III) and/or (IV) above with an alkali metal hydroxide or an alkaline earth metal hydroxide in an ether type solvent. The β-keto-carboxylic acid derivatives (II) used as starting materials can easily be prepared by known methods, for example, by the addition reaction of a carbon tetrahalide to an α-acyl-65-unsaturated carboxylate which is obtainable by condensing 3-methyl-2-buten -1-ol with an acetoacetic acid ester derivative. Other starting materials, cyclopropane derivatives (III) and (IV), can be prepared by treating the above-described β-keto-carboxylic acid derivatives (II) with a weak base.

Examples of the compounds represented by the formula (II) above are methyl 2-acetyl-4,6,6,6-tetrachloro-3,3-dimethylhexanoate, ethyl 2-acetyl-4,6,6,6-tetrachloro-3,3-dimethylhexanoate, isopropyl 2-acetyl-4,6,6,6-tetrachloro-3,3-dimethylhexanoate, n-butyl 2-acetyl-4,6,6,6-tetrachloro-3,3-dimethylhexanoate, ethyl 2-propionyl-4,6,6,6-tetrachloro-3,3-dimethylhexanoate, ethyl 2-benzoyl-4,6,6,6-tetrachloro-3,3-dimethylhexanoate, ethyl 2-acetyl-4,6,6,6-tetrachloro-3-methylhexanoate, methyl 2-acetyl-4,6,6,6-tetrachloro-3-phenylhexanoate, ethyl 2-acetyl-4,6,6,6-tetrachloro-3-phenylhexanoate, methyl 2-acetyl-4-bromo-6,6,6-trichloro-3,3-dimethylhexanoate, ethyl 2-acetyl-4-bromo-6,6,6-trichloro-3,3-dimethylhexanoate, ethyl 2-acetyl-4,6,6,6-tetrabromo-3,3-dimethylhexanoate, ethyl 2-acetyl-4,6-dibromo-6,6-dichloro-3,3-dimethylhexanoate, ethyl 2-acetyl-4,6-dichloro-6,6-defluoro-3,3-dimethylhexanoate, and the like.

In the process of the present invention, a compound of the formula (II), (III), or (IV), or a mixture thereof, is treated with an alkali metal hydroxide or an alkaline earth metal hydroxide in an ether type solvent. Examples of the ether type solvent are those easily available as industrial solvents such as diethyl ether, dibutyl ether, tetrahydrofuran, dioxane, dimethoxyethane, and the like, but it is preferred to use tetrahydrofuran from the standpoint of ease in handling and reaction efficiency. Also, in addition to the ether type solvent, any solvent which does not adversely affect the reaction can be used as a mixture with the ether type solvent. Examples of the solvents which can be used in combination with the ether type solvent are hydrocarbons such as benzene, toluene, and the like, and N,N-dimethylformamide and the like. Solvents which adversely affect the reaction are protonic solvents such as alcohols. Examples of the alkali metal hydroxides or alkaline earth metal hydroxides are potassium hydroxide, sodium hydroxide, barium hydroxide, lithium hydroxide, and the like. These bases are generally used in an amount in excess of 2 mol equivalents, preferably 3 to 5 mol equivalents, based on the starting compound of the formula (II), or in an amount in excess of 1 mol equivalent, preferably 2 to 4 mol equivalents, based on the starting compound of the formula (III) or (IV). The reaction temperature will preferably be within the range from 0° C. to the reflux temperature of the solvent, taking into consideration the reaction rate and stability of the product to be obtained.

In the process of this invention, water or an alcohol is formed as the reaction proceeds, and to facilitate the desired reaction it is preferable to remove from the reaction system the water or alcohol thus formed. For this purpose, the water can be removed with a Dean-Stark water trap or, alternatively, a molecular sieve can be present in the reaction system to adsorb both the water and alcohol formed during the reaction.

The present invention also includes a process for preparing a 2-(2,2-dihalovinyl)cyclopropanecarboxylic acid using, as a starting material, a compound of the formula (II) and isolating the compound of the formula (III) and/or (IV). The step for producing the compound of the formula (III) or (IV) from the compound of the formula (II) comprises, as an essential requirement, treating the compound of the formula (II) with a base.

As the base, alkali metal hydroxides, alkaline earth metal hydroxides, alkali metal alkoxides, organic amines, and the like can preferably be used. In carrying out the reaction, the use of a solvent is preferred. Examples of the solvent which can be used are alcohols, benzene, xylene, ethers, and the like.

The starting compound of the formula (III) can easily be synthesized by, for example, treating a compound of the formula (II) above with an alkali metal alkoxide in an alcohol or treating a compound of the formula (II) with an alkali metal hydroxide in an ether type solvent. Also, the starting compound of the formula (IV) can be synthesized by treating a compound of the formula (II) above with a weak base such as barium hydroxide in an alcohol or treating a compound of the formula (II) with an alkali metal hydroxide in benzene. The amount of the base used in this step varies depending upon the type of the base, but is generally more than 1 mol, preferably in the range of 2 to 5 mols, per mol of the starting material of the formula (II). The reaction temperature is not critical, and the reaction can be conducted at a temperature of from 0° C. to 150° C. or higher, for example 50° C. to 100° C., but is conveniently carried out at the relux temperature of the solvent. Whether the compound of the formula (III) or (IV) will be obtained depends on the type and amount of the base, the type of the solvent, the reaction temperature, and the reaction time. However, the synthesis of the desired compounds of the formula (I) can suitably be attained from the thus formed compounds (III) and (IV) under the reaction conditions previously described.

The present invention is further illustrated in greter detail by the following Examples. Temperatures are in degrees centigrade. Tetramethylsilane was employed as an internal standard for the nmr spectra. In the nmr data the abbreviations have the following significance: s, singlet; d, doublet; t, triplet; q, quartet; m, multiplet. Any of these abbreviations may be preceded by b for broad or d for double, for example, dd, double doublet; bt broad triplet.

EXAMPLE 1

Preparation of Ethyl 1-Acetyl-2-(2,2,2-trichloroethyl)-3,3-dimethylcyclopropanecarboxylate A. With Sodium Ethoxide To make the starting material, cupric acetate (0.195 g) and 0.309 g of n-butylamine were dissolved in 3.3 g of dimethylformamide, and a solution of 3.0 g of ethyl 2-acetyl-3,3-dimethyl-4-pentenoate dissolved in 4.8 g of carbon tetrachloride was added to the mixture. The reaction system was purged with argon, sealed, and then heated at 120° C. for 23 hours. After completion of the heating, the reaction mixture was diluted with diethyl ether and washed successively with water, 1N hydrochloric acid, aqueous sodium bicarbonate, and aqueous sodium chloride. The mixture was then dried over anhydrous magnesium sulfate and distilled to give 3.6 g (conversion ratio, 89%; conversion yield, 75%) of ethyl 2-acetyl-4,6,6,6-tetrachloro-3,3-dimethylhexanoate, boiling point 108°-120° C./0.1 mmHg.

Sodium (0.15 g) was dissolved in 10 ml of absolute ethanol, and 2.29 g of ethyl 2-acetyl-4,6,6,6-tetrachloro-3,3-dimethylhexanoate was added, while the reaction mixture was cooled with ice. After stirring at room temperature for 15 minutes, the mixture was rendered neutral with an ethereal solution of hydrogen chloride, while cooled with ice, and then the solvent was distilled off. The resulting residue was dissolved in diethyl ether, and the solution was washed with water, dried over anhydrous magnesium sulfate, and distilled to give an oily substance having a boiling point of 108°-112° C./0.6 mmHg. Purification by column chromatography (silica gel-benzene) gave 1.1 g (50% yield) of ethyl 1-acetyl-2-(2,2,2-trichloroethyl)-3,3-dimethylcyclopropanecarboxylate.

NMR Absorption Spectrum of Product (CCl$_4$,δ): 4.10 (q, 2H), 3.23-2.63 (m, 2H), 2.16 (s, 3H), 2.23-1.93 (m, 1H), 1.23 (t, 3H), 1.23 (bs, 3H), 1.06 (bs, 3H).

B. With Barium Hydroxide

Anhydrous barium hydroxide (0.86 g) was added to 10 ml of absolute ethanol, and 1.76 g of ethyl 2-acetyl-4,6,6,6-tetrachloro-3,3-dimethylhexanoate was then added thereto, while the reaction mixture was cooled with ice. After stirring at room temperature for 2 hours, the mixture was rendered neutral with an ethereal hydrogen chloride, while cooled with ice, the solvent was distilled off. The resulting residue was dissolved in diethyl ether, and the solution was washed successively with water, aqueous sodium bicarbonate, and aqueous sodium chloride and dried over anhydrous magnesium sulfate. The solvent ws distilled off, and the residue was purified by column chromatography (silica gel-benzene) to give 1.3 g (82% yield) of ethyl 1-acetyl-2-(2,2,2-trichloroethyl)-3,3-dimethylcyclopropanecarboxylate.

The NMR spectrum of the product thus obtained was found to be quite consistent with that of the product obtained in Example 1A.

C. With Sodium Hydroxide

Sodium hydroxide (1.0 g) and 4 ml of anhydrous benzene were charged into a dry flask, and the system was purged with argon. A solution of 1.76 g of ethyl 2-acetyl-4,6,6,6-tetrachloro-3,3-dimethylhexanoate in 2 ml of anhydrous benzene was then added, while the mixture was cooled with ice. The resulting mixture was stirred with cooling for 1 hour and then stirred at room temperature for an additional 2 hours. Benzene (5 ml) was added thereto, and the resulting mixture was heated under reflux for 5 hours, while the water which had formed during the reaction was distilled out as an azeotropic mixture. After completion of the heating, the mixture was rendered acidic by the addition of a solution of dry hydrogen chloride in dioxane. The precipitated solid was removed by filtration and the filtrate was concentrated under reduced pressure. The resulting residue was purified by column chromatography (silica gel-benzene) to give 0.65 g (41% yield ) of ethyl 1-acetyl-2(2,2,2-trichloroethyl)-3,3-dimethylcyclopropanecarboxylate.

The NMR spectrum of the product thus obtained was found to be quite consistent with that of the product obtained in Example 1A.

EXAMPLE 2

Preparation of Ethyl 1-Acetyl-2-(2,2-dichlorovinyl)-3,3-dimethylcyclopropanecarboxylate Sodium (0.5 g) was dissolved in 37 ml of absolute ethanol, and 2.9 g of ethyl 2-acetyl-4,6,6,6-tetrachloro-3,3-dimethylhexanoate was added thereto. The mixture was stirred at room temperature for 30 minutes and then heated at a temperature of 50° C. for 24 hours with stirring. The mixture was rendered neutral with an ethereal solution of hydrogen chloride, while cooled with ice and the solvent was distilled off. The resulting residue was dissolved in diethyl ether, and the solution was washed with water, dried over anhydrous magnesium sulfate, and distilled to give 2.01 g (88% yield) of ethyl 1-acetyl-2-(2,2-dichlorovinyl)3,3-dimethylcyclopropanecarboxylate.

NMR Absorption Spectrum of Product (CCl$_4$,δ): 5.87, 5.80 (dd, 1H), 4.20 (bq, 2H), 2.60, 2.53 (dd, 1H), 2.20 (bs, 3H), 1.50–1.00 (m, 9H).

EXAMPLE 3

Preparation of 1-Acetyl-2-(2,2-dichlorovinyl)-3,3-dimethylcyclopropanecarboxylic Acid

A. From Ethyl 2-Acetyl-4,6,6,6-tetrachloro-3,3-dimethylhexanoate

Sodium hydroxide powder (0.58 g) and 10 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was then added, while the reaction mixture was cooled with ice-sodium chloride. The cooled mixture was stirred for 1 hour, at room temperature for 3 hours, and then heated at a temperature of 50° C. for 42 hours, while stirring continued. The solvent was distilled off, and the resulting residue was dissolved in 10 ml of a 1N aqueous solution of sodium hydroxide. After removal of any water-insoluble materials by extraction with diethyl ether, the alkaline aqueous solution was rendered acidic with 1N hydrochloric acid and extraced with diethyl ether. The extract was dried over anhydrous magnesium sulfate, and the ether was distilled off to give 1.03 g (81% yield) of 1-acetyl-2-(2,2-dichlorovinyl)-3,3-dimethylcyclopropanecarboxylic acid.

NMR Absorption Spectrum of Product (CDCl$_3$,δ): 12.4 (bs, 1H), 5.97, 5.93 (dd, 1H), 2.74, 2.67 (dd, 1H), 2.40 (bs, 3H), 1.46–1.06 (m, 6H).

B. From Isopropyl 2-Acetyl-4,6,6,6-tetrachloro-3,3-dimethylhexanoate

Sodium hydroxide powder (0.58 g) and 10 ml of anhydrous tetrahydrofuran were charged into a dry flask, and the system was purged with argon. Isopropyl 2-acetyl-4,6,6,6-tetrachloro-3,3-dimethylhexanoate (1.83 g) was then added to the mixture, while the reaction mixture was cooled with ice-sodium chloride, and the resulting mixture was stirred for 1 hour. Thereafter, the mixture was stirred at room temperature for 4 hours and then heated at 50° C. for 40 hours with stirring. The solvent was distilled off, and the resulting residue was dissolved in 10 ml of a 1N aqueous solution of sodium hydroxide. After removal of any water-insoluble materials by extraction with diethyl ether, the alkaline aqueous solution was rendered acidic with 1N hydrochloric acid and extracted with diethyl ether. The extract was dried over anhydrous magnesium sulfate, and the ether was distilled off to give 0.85 g (67% yield) of 1-acetyl-2-(2,2-dichlorovinyl)-3,3-dimethylcyclopropanecarboxlic acid.

The NMR spectrum of the product thus obtained was found to be quite consistent with that of the product obtained in Example 3A.

EXAMPLE 4

Preparation of 2-(2,2-Dichlorovinyl)-3,3-dimethylcyclopropanecarboxylic Acid

A. From Ethyl 1-Acetyl-2-(2,2-dichlorovinyl)-3,3-dimethylcyclopropanecarboxylate Sodium hydroxide powder (0.09 g) and 2 ml of anhydrous tetrahydrofuran were charged into a dry flask, and the system was purged with argon. Ethyl 1-acetyl-2-(2,2-dichlorovinyl)-3,3-dimethylcyclopropanecarboxylate (0.28 g) was then added, and the resulting mixture was stirred first for 2 hours at room temperature, then at 50° C. for 16 hours. The reaction mixture was then rendered acidic with 10% aqueous hydrogen chloride, while cooled with ice, and extracted with diethyl ether. The extract was dried over anhydrous magnesium sulfate, and the solvent was distilled off to give 0.13 g (62% yield) of 2-(2,2-dichlorovinyl)-3,3-dimethylcyclopropanecarboxylic acid.

NMR Absorption Spectrum of Product (CDCl$_3$,δ): 10.6 (bs, 1H), 6.20, 5.61 (dd, 1H), 2.44–1.57 (m, 2H), 1.47–1.05 (m, 6H).

From the different absorption values of the olefinic hydrogens at 6.20 and 5.61 in the above NMR absorption spectrum the product obtained was found to contain cis- and trans-forms at a ratio of 4:6.

B. From 1-Acetyl-2-(2,2-dichlorovinyl)-3,3-dimethylcyclopropanecarboxylic Acid Sodium hydroxide powder (0.36 g) and 1 ml of anhydrous tetrahydrofuran were charged into a dry flask, and the system was purged with argon. A solution of 0.65 g of 1-acetyl-2-(2,2-dichlorovinyl)-3,3-dimethylcyclopropanecarboxylic acid in 2 ml of tetrahydrofuran was then added, and the resulting mixture was stirred for 10 minutes at room temperature, then at 50°-60° C. for 15 hours with stirring. The reaction mixture was then dissolved in 2 ml of water, and the solution was rendered acidic with 10% hydrochloric acid, while cooled with ice, and extracted with diethyl ether. The extract was dried over anhydrous magnesium sulfate, and the solvent was distilled off to give 0.44 g (82% yield) of 2-(2,2-dichlorovinyl)-3,3-dimethylcyclopropanecarboxylic acid.

The NMR spectrum of the product thus obtained was found to be quite consistent with that of the product obtained in Example 4A.

The product was found to contain cis- and trans-forms in a ratio of 4.5:5.5.

C. From Ethyl 1-Acetyl-2-(2,2,2-trichloroethyl)-3,3-dimethylcyclopropanecarboxylic Acid Sodium hydroxide powder (0.4 g) and 2 ml of anhydrous tetrahydrofuran were charged into a dry flask, and the system was purged with argon. A solution of 0.79 g of ethyl 1-acetyl-2-(2,2,2-trichloroethyl)-3,3-dimethylcyclopropanecarboxylate in 1 ml of tetrahydrofuran was added, while the mixture was cooled with ice-sodium chloride. The resulting mixture was stirred for 2 hours at room temperature, and then heated under reflux for 8 hours while the water formed during the reaction was distilled off. After completion of the reaction, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.3 g (57% yield) of 2-(2,2-dichlorovinyl)-3,3-dimethylcyclopropanecarboxylic acid.

The NMR spectrum of the product thus obtained was found to be quite consistent with that of the product obtained in Example 4A.

D. From a Mixture of Ethyl 1-Acetyl-2-(2,2,2-trichloroethyl)- and 1-Acetyl-2-(2,2-dichlorovinyl)-3,3-dimethylcyclopropenecarboxylates Sodium hydroxide powder (0.44 g) and 4 ml of anhydrous tetrahydrofuran were charged into a dry flask, and the system was purged with argon. A solution of 0.63 g of ethyl 1-acetyl-2-(2,2,2-trichloroethyl)-3,3-dimethylcyclopropanecarboxylate and 0.56 g of ethyl 1-acetyl-2-(2,2-dichlorovinyl)-3,3-dimethylcyclopropanecarboxylate in 1 ml of tetrahydrofuran was added to the mixture, while the mixture was cooled with ice. The resulting mixture was stirred at room temperature for 2 hours and then heated under reflux for 10 hours, while the water formed during the reaction was distilled out as an azeotropic mixture. Thereafter, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.5 g (60% yield) of 2-(2,2-dichlorovinyl)-3,3-dimethylcyclopropanecarboxylic acid.

The NMR spectrum of the product thus obtained was found to be quite consistent with that of the product obtained in Example 4A.

E. From Ethyl 2-Acetyl-4,6,6,6-tetrachloro-3,3-dimethylhexanoate (1) Sodium hydroxide powder (1.0 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added while the mixture was cooled with ice-sodium chloride. The mixture was stirred with cooling for 1 hour, at room temperature for 2 hours, and then heated under reflux for 7 hours, while the water formed during the reaction was distilled out as an azeotropic mixture. After completion of the reaction, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.82 g (78% yield) of 2-(2,2-dichlorovinyl)-3,3-dimethylcyclopropanecarboxylic acid.

The NMR spectrum of the product thus obtained was found to be quite consistent with that of the product obtained in Example 4A and showed that the product contained cis- and trans-forms in a ratio of 4.3:5.7.

(2) Sodium hydroxide powder (1.0 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of anhydrous tetrahydrofuran was added while the mixture was cooled with ice-sodium chloride. The resulting mixture was stirred for 1 hour with cooling, and then for 2 hours at room temperature. Thereafter, 3 ml of tetrahydrofuran and 2 ml of benzene were added, and the resulting mixture was heated under reflux for 8 hours, while the water formed during the reaction was distilled out as an azeotropic mixture. After completion of the reaction, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.77 g (74% yield) of 2-(2,2-dichlorovinyl)-3,3-dimethylcyclopropanecarboxylic acid.

The NMR spectrum of the product thus obtained was found to be quite consistent with that of the product obtained in Example 4A and showed that the product contained cis- and trans-forms in a ratio of about 1:1.

(3) Sodium hydroxide powder (0.5 g) and 4 ml of anhydrous dimethoxyethane were charged into a dry flask, and the system was purged with argon. A solution of 1.76 g of ethyl 2-acetyl-4,6,6,6-tetrachloro-3,3-dimethylhexanoate in 2 ml of dimethoxyethane was added while the mixture was cooled with ice-sodium chloride. The resulting mixture was stirred for 1 hour with cooling, then at room temperature for 2 hours. Thereafter, 0.5 g of sodium hydroxide powder was added to the mixture, and the reaction temperature of the mixture was increased to 50°–80° C., at which temperature the mixture was stirred for 37 hours. The reaction mixture was then diluted with water, and any water-insoluble materials were removed by extraction with diethyl ether. The aqueous layer was rendered acidic with 1N hydrochloric acid and extracted with diethyl ether. The ether extract was dried over anhydrous magnesium sulfate, and the solvent was distilled off to give 0.72 g (69% yield) of 2-(2,2-dichlorovinyl)-3,3-dimethylcyclopropanecarboxylic acid.

The NMR spectrum of the product thus obtained was found to be quite consistent with that of the product obtained in Example 4A.

(4) Sodium hydroxide powder (1.0 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added while the mixture was cooled with ice-sodium chloride. The resulting mixture was stirred for 1 hour with cooling, then at room temperature for 2 hours. After heating at 50°–55° C. for 41 hours, the mixture was worked up in the same manner as described in Example 4E(3) to give 0.7 g (67% yield) of 2-(2,2-dichlorovinyl)-3,3-dimethylcyclopropanecarboxylic acid.

The NMR spectrum of the product thus obtained was found to be quite consistent with that of the product obtained in Example 4A.

(5) Sodium hydroxide powder (1.0 g) and 6 ml of anhydrous tetrahydrofuran were charged into a dry flask, and the system was purged with argon. A solution of 2.07 g of ethyl 2-benzoyl-4,6,6,6-tetrachloro-3,3-dimethylhexanoate in 2 ml of tetrahydrofuran was added while the mixture was cooled with ice-sodium chloride. The reaction mixture was stirred with cooling for 1 hour, then at room temperature for 2 hours. The resulting mixture was then heated under reflux for 7 hours while the water formed during the reaction was distilled off as an azeotropic mixture. After completion of the reaction, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.43 g (41% yield) of 2-(2,2-dichlorovinyl)-3,3-dimethylcyclopropanecarboxylic acid.

The NMR spectrum of the product thus obtained was found to be quite consistent with that of the product obtained in Example 4A and showed that the product contained cis- and trans-forms in a ratio of 3.7:6.3.

(6) Potassium hydroxide powder (1.4 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added while the mixture was cooled with ice-sodium chloride. The resulting mixture was stirred with cooling for 1 hour, then at room temperature for 2 hours. The resulting mixture was then heated under reflux for 10 hours while the water formed during the reaction was distilled off as an azeotropic mixture. After completion of the reaction, the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 0.3 g (29% yield) of 2-(2,2-dichlorovinyl)-3,3-dimethylcyclopropanecarboxylic acid.

The NMR spectrum of the product thus obtained was found to be quite consistent with that of the product obtained in Example 4A and showed that the product contained cis- and trans-forms in a ratio of 1:1.

(7) Anhydrous barium hydroxide (4.27 g) and 6 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added while the mixture was cooled with ice-sodium chloride. The resulting mixture was stirred with cooling for 30 minutes, then at room temperature for 2 hours. The resulting mixture was then heated under reflux for 20 hours while the water formed during the reaction was distilled off as an azeotropic mixture. After completion of the reaction, an aqueous solution of sodium hydroxide was added to the mixture, and any water-insoluble materials were removed by extraction with diethyl ether. The aqueous layer was rendered acidic with dilute hydrochloric acid and extracted with diethyl ether. The ether extract was dried over anhydrous magnesium sulfate, and the solvent was distilled off to give 0.18 g (17% yield) of 2-(2,2-dichlorovinyl)-3,3-dimethylcyclopropanecarboxylic acid.

The NMR spectrum of the product thus obtained was found to be quite consistent with that of the product obtained in Example 4A.

EXAMPLE 5

Preparation of 2-(2,2-Dichlorovinyl)-3-phenylcyclopropanecarboxylic Acid

Sodium hydroxide (1.0 g) and 4 ml of anhydrous tetrahydrofuran were charged into a dry flask, and the system was purged with argon. A solution of 2.0 g of ethyl 2-acetyl-4,6,6,6-tetrachloro-3-phenylhexanoate in 2 ml of tetrahydrofuran was added while the mixture was cooled with ice-sodium chloride. The resulting mixture was stirred with cooling for 1 hour, then at room temperature for 2 hours. The resulting mixture was then heated under reflux for 10 hours, while the water formed during the reaction was distilled off as an azeotropic mixture. After completion of the reaction the reaction mixture was diluted with water, and any water-insoluble materials were removed by extraction with diethyl ether. The aqueous layer was rendered acidic with 1N hydrochloric acid and extracted with diethyl ether. The ether extract was treated with activated carbon, dried over anhydrous magnesium sulfate, and the solvent was distilled off to give 1.2 g (93% yield) of 2-(2,2-dichlorovinyl)-3-phenylcyclopropanecarboxylic acid.

The NMR spectrum of the product thus obtained was found to comprise at least 3 structural isomers. These structural isomers could be distinguished from each other by different absorption values in the following NMR absorption spectrum (CDCl$_3$,δ) due to an olefinic hydrogen: 11.1 (bs, 1H), 7.2 (bs, 5H), 6.08 (d, 0.28H), 5.50 (d, 0.44), 5.17 (d, 0.28H), 3.20–2.0 (m, 3H).

By the methods exemplified above a great variety of compounds of formula (II), (III), or (IV) may be converted to acids of formula (I), for example, methyl 2-acetyl-4-bromo-6,6,6-trichloro-3,3-dimethylhexanoate may be converted to 2-(2,2-dichlorovinyl)-3,3-dimethylcyclopropanecarboxylic acid, and ethyl 2-(2,2,2-tribromoethyl)-3,3-dimethyl-2-propionylcyclopropanecarboxylate to ethyl 2-(2,2-dibromovinyl)-3,3-dimethylcyclopropanecarboxylic acid.

EXAMPLE 6

Preparation of Benzyl 2-(2,2-Dichlorovinyl)-3,3-dimethylcyclopropanecarboxylate

A. Sodium hydroxide powder (1.0 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added while the mixture was cooled with an ice-salt mixture. The reaction mixture was stirred for 1 hour with cooling, for 2 hours at room temperature, and then for 14 hours at the reflux temperature. After the reaction mixture was cooled to room temperature, then 1.76 g of benzyl bromide was added, and the reaction mixture was heated under reflux for 23 hours. The reaction mixture was acidified with an ethereal solution of hydrogen chloride while cooled with ice, and then washed with water. The organic layer was dried over anhydrous magnesium sulfate and distilled to give 0.8 g (54% yield) of benzyl 2-(2,2-dichlorovinyl)-3,3-dimethylcyclopropanecarboxylate, boiling point 105°–115° C./0.1 mmHg.

NMR Absorption Spectrum of the Product (CCl$_4$,δ): 7.27 (bs, 5H), 6.23, 5.53 (dd, 1H), 5.05 (bs, 2H), 2.37, 1.43 (m, 2H), 1.40, 0.93 (m, 6H).

From the ratio of absorption heights of the olefinic hydrogens at 6.23 and 5.53 in the NMR spectrum, the ratio of cis- and trans-isomers was found to be 38:62.

B. Sodium hydroxide powder (1.0 g) and 4 ml of anhydrous tetrahydrofuran were charged into a dry flask, and the system was purged with argon. A solution of 1.76 g of ethyl 2-acetyl-4,6,6,6-tetrachloro-3,3-dimethylhexanoate in 2 ml of tetrahydrofuran was added to the mixture under cooling with ice-salt mixture. The reaction mixture was stirred for 1 hour with cooling, for 2 hours at room temperature, and then for 17 hours at the reflux temperature. After the reaction mixture was cooled to room temperature, 1.27 g of benzyl chloride was added to the mixture, and the resulting mixture was heated to reflux for 25 hours. Thereafter, tetrahydrofuran was distilled off, and 10 ml of toluene was added to the residue. The mixture was again heated under reflux for 37 hours. After completion of the reaction, the mixture was acidified by addition of an ethereal solution of hydrogen chloride, while cooled with ice, and then washed with water. The organic solution was dried over anhydrous magnesium sulfate and distilled to afford 0.76 g (51% yield) of benzyl 2-(2,2-dichlorovinyl)-3,3-dimethylcyclopropanecarboxylate, boiling point 105°–115° C./0.1 mmHg.

The NMR absorption spectrum of the product was identical with that obtained in Example 6A.

In a similar manner, 3-phenoxybenzylchloride is reacted with the sodium salt of 2-(2,2-dichlorovinyl)-3,3-dimethylcyclopropanecarboxylic acid, prepared by the process of this invention, to yield 3-phenoxybenzyl 2-(2,2-dichlorovinyl)3,3-dimethylcyclopropanecarboxylate.

It is apparent that examples of the process of this invention may be multiplied indefinitely without departing from the scope of the invention in the following claims.

We claim:

1. A process for preparing a 2-(2,2-dihalovinyl)cyclopropanecarboxylic acid of the formula

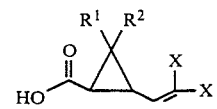

wherein R$^1$ and R$^2$ each independently is hydrogen or a hydrocarbon group, and X is halogen, which comprises reacting an α-acyl-γ-halocarboxylic acid derivative of the formula

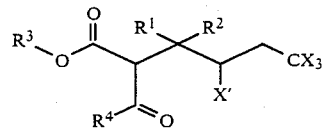

wherein R$^1$, R$^2$ and X are as defined above, R$^3$ is hydrogen or lower alkyl, X' is halogen of atomic number equal to or higher than X, and R$^4$ is a hydrogen, or lower alkyl; with an alkali metal hydroxide or alkaline earth metal hydroxide in an ether type solvent.

2. A process of claim 1 in which R$^1$ and R$^2$ each independently is hydrogen, lower alkyl, or phenyl, X is chlorine, bromine, or fluorine, and X' is chlorine or bromine.

3. The process of claim 2 in which R$^1$, R$^2$, and R$^4$ each is methyl.

4. The process of claim 3 in which X and X' each is chlorine.

5. Process as in claim 4 in which the amount of base is in excess of 2 mol equivalents.

6. Process as in claim 5 in which the amount of base is at least 3 mol equivalents.

7. Process as in claim 5 in which said base is in sodium hydroxide and said solvent is tetrahydrofuran.

8. Process as in claim 1 in which said hydroxide is reacted with said α-acyl-γ-halocarboxylic acid derivative in admixture with a 1-acyl-2-(2,2,2-trihaloethyl)cyclopropane derivative of the formula

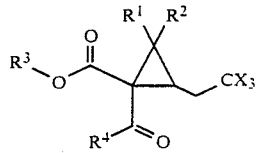

9. A process for preparing a 2-(2,2-dihalovinyl)cyclopropanecarboxylic acid of the formula

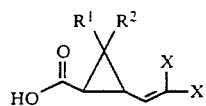

wherein $R^1$ and $R^2$ each independently is hydrogen or a hydrocarbon residual group, and X is halogen, which comprises reacting a 1-acyl-2-(2,2-trihaloethyl)cyclopropane derivative of the formula

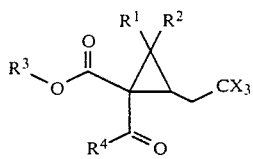

wherein $R^1$, $R^2$ and X are as defined above, $R^3$ is hydrogen or lower alkyl, and $R^4$ is hydrogen or lower alkyl; or with an alkali metal hydroxide or alkaline earth metal hydroxide in an ether type solvent.

10. Process as in claim 9 in which the amount of base is at least 2 mol equivalents.

11. Process as in claim 10 in which said base is sodium hydroxide and said solvent is tetrahydrofuran.

* * * * *